US012648935B2

(12) United States Patent
Baylink

(10) Patent No.: US 12,648,935 B2
(45) Date of Patent: Jun. 9, 2026

(54) **COMPOSITIONS AND METHODS FOR AMELIORATING *HELICOBACTERACEAE* INFECTIONS**

(71) Applicant: University of Oregon, Eugene, OR (US)

(72) Inventor: Arden Baylink, Pullman, WA (US)

(73) Assignee: University of Oregon, Eugene, OR (US)

( * ) Notice: Subject to any disclaimer, the term of this patent is extended or adjusted under 35 U.S.C. 154(b) by 403 days.

(21) Appl. No.: 18/356,182

(22) Filed: Jul. 20, 2023

(65) Prior Publication Data

US 2024/0041844 A1 Feb. 8, 2024

Related U.S. Application Data

(60) Provisional application No. 63/392,784, filed on Jul. 27, 2022.

(51) Int. Cl.

| | |
|---|---|
| ***A61K 31/437*** | (2006.01) |
| ***A61K 31/155*** | (2006.01) |
| ***A61K 31/17*** | (2006.01) |
| ***A61K 31/222*** | (2006.01) |
| ***A61K 31/345*** | (2006.01) |
| ***A61K 31/351*** | (2006.01) |
| ***A61P 31/04*** | (2006.01) |

(52) U.S. Cl.

CPC .......... *A61K 31/437* (2013.01); *A61K 31/155* (2013.01); *A61K 31/17* (2013.01); *A61K 31/222* (2013.01); *A61K 31/345* (2013.01); *A61K 31/351* (2013.01); *A61P 31/04* (2018.01)

(58) Field of Classification Search

CPC .... A61K 31/155; A61K 31/17; A61K 31/222; A61K 31/345; A61K 31/351; A61K 31/437; A61P 31/04

See application file for complete search history.

(56) References Cited

U.S. PATENT DOCUMENTS

| | | | |
|---|---|---|---|
| 6,215,016 | B1 | 4/2001 | Kawai et al. |
| 7,166,612 | B2 | 1/2007 | Flaumenhaft |

FOREIGN PATENT DOCUMENTS

| | | | |
|---|---|---|---|
| WO | WO 01/74790 A2 | 10/2001 | |
| WO | WO 2013/091062 A2 | 6/2013 | |

OTHER PUBLICATIONS

Bhat et al., "Synthesis and in vitro evaluation of substituted 3-cinnamoyl-4-hydroxy-pyran-2-one (CHP) in pursuit of new potential antituberculosis agents," *Med. Chem. Commun.*, May 30, 2018, 9:165-172.

Nelson et al., "Measurement of Peroxiredoxin Activity," *Curr Protoc Toxicol.*, Aug. 15, 2011, Author Manuscript published Jul. 8, 2013, 33 pages.

*Primary Examiner* — Umamaheswari Ramachandran
(74) *Attorney, Agent, or Firm* — KLARQUIST SPARKMAN, LLP

(57) ABSTRACT

A pharmaceutical composition includes a Helicobacteraceae enzyme inhibitor and a pharmaceutically acceptable carrier. The enzyme inhibitor may inhibit peroxiredoxin, such as alkyl hydroperoxide reductase C, thiol-specific peroxidase, bacterioferritin comigratory protein, or any combination thereof. A method for ameliorating a Helicobacteraceae infection includes administering to a subject a therapeutically effective amount of a pharmaceutical composition including a Helicobacteraceae enzyme inhibitor and a pharmaceutically acceptable carrier.

16 Claims, 2 Drawing Sheets

COMPOSITIONS AND METHODS FOR AMELIORATING *HELICOBACTERACEAE* INFECTIONS

CROSS-REFERENCE TO RELATED APPLICATION

This application claims the benefit of the earlier filing date of U.S. Provisional Application No. 63/392,784, filed Jul. 27, 2022, which is incorporated by reference in its entirety herein.

FIELD

Compositions and methods for ameliorating Helicobacteraceae infections are disclosed.

SUMMARY

Embodiments of a pharmaceutical composition include a Helicobacteraceae enzyme inhibitor and a pharmaceutically acceptable carrier, wherein the pharmaceutical composition is formulated to release the Helicobacteraceae enzyme inhibitor in a subject's stomach and/or duodenum. In some embodiments, the Helicobacteraceae enzyme inhibitor is a peroxiredoxin inhibitor. In certain implementations, the peroxiredoxin inhibitor inhibits alkyl hydroperoxide reductase C (AhpC), thiol-specific peroxidase (Tpx), bacterioferritin comigratory protein (BCP), or any combination thereof. The aforementioned are all enzymes possessed by Helicobacteraceae organisms that are within the larger family of enzymes known as peroxiredoxins. In any of the foregoing or following embodiments, the Helicobacteraceae enzyme inhibitor may be a compound, or a pharmaceutically acceptable salt, solvate or hydrate thereof, wherein the compound has a structure according to formula I', formula II', formula III', compound IV, formula V', formula VI', or any combination thereof:

(I')

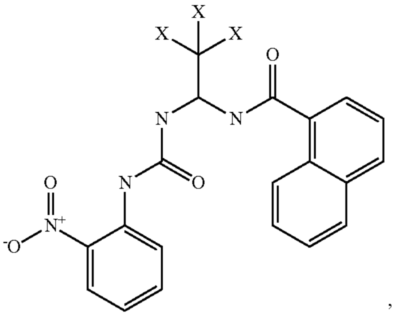

, (II')

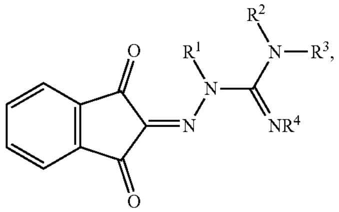

-continued (III')

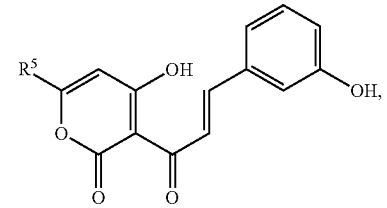

(IV')

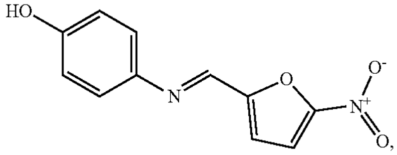

(V')

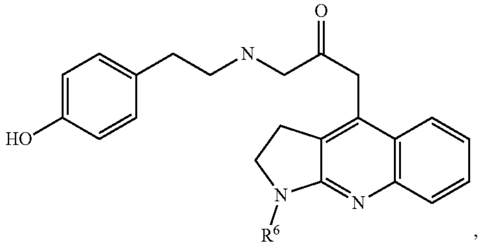

, (VI')

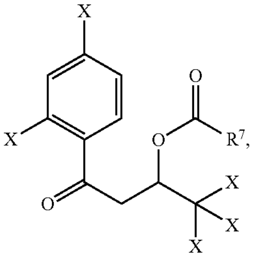

wherein each X independently is halo; and $R^1$-$R^7$ independently are H or $C_1$-$C_5$ alkyl.

In some embodiments, the compound is compound I, compound II, compound III, compound IV, compound V, compound VI, or any combination thereof:

(I)

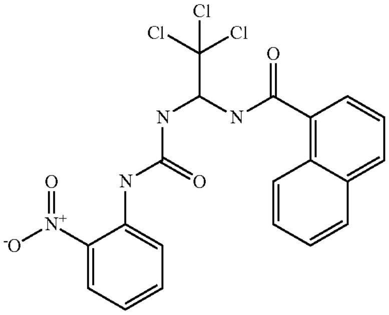

, (II)

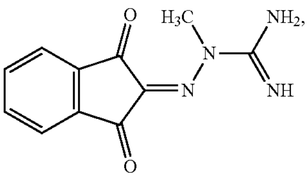

-continued (III)

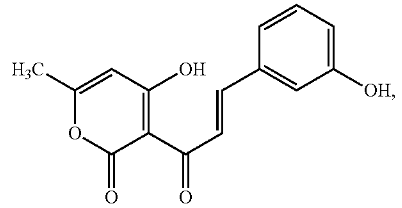

(IV)

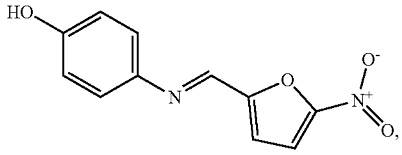

(V)

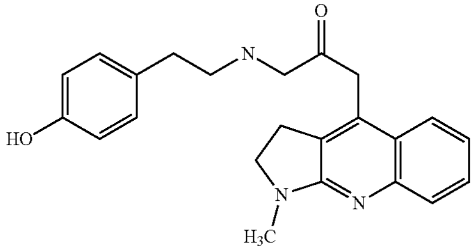

, (VI)

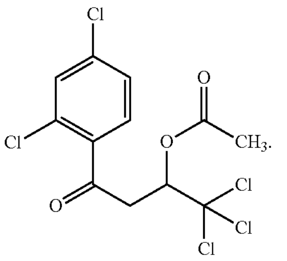

In some embodiments, the pharmaceutical composition comprises compound I, compound II, or a combination thereof. In certain implementations, compound I is a stereoisomer having the structure (IA)

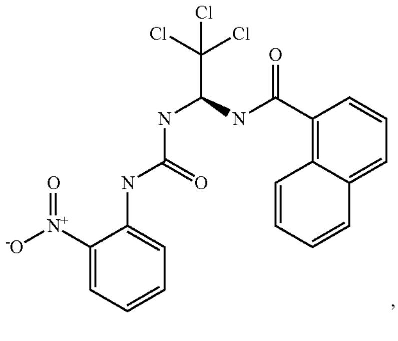

, and/or compound VI is a stereoisomer having the structure (VIA)

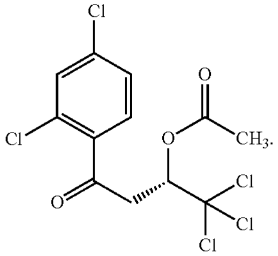

In any of the foregoing or following embodiments, the pharmaceutical composition may be formulated for parenteral or oral administration. In some implementations, the pharmaceutical composition is formulated into a solid dosage form for oral administration. Advantageously, the oral dosage form is formulated to release the Helicobacteraceae enzyme inhibitor in a subject's stomach and/or duodenum. In some embodiments, oral dosage form further comprises a coating or a capsule shell encapsulating the pharmaceutical composition, wherein the coating or capsule shell is an immediate release coating or capsule shell formulated to dissolve in the subject's stomach and/or duodenum.

A method for inhibiting an enzyme produced by a Helicobacteraceae species includes contacting the enzyme with an effective amount of compound I (or the stereoisomer compound IA), compound II, compound III, compound IV, compound V, compound VI (or the stereoisomer compound VIA), or any combination thereof. In some embodiments, contacting is performed in vivo.

A method for ameliorating a Helicobacteraceae infection includes administering to a subject a therapeutically effective amount of a pharmaceutical composition as disclosed herein. The method may further include identifying the subject as having a Helicobacteraceae infection prior to administering the therapeutically effective amount of the pharmaceutical composition. In any of the foregoing or following embodiments, the therapeutically effective amount may be administered at periodic intervals for an effective period of time to ameliorate the Helicobacteraceae infection. In some embodiments, the therapeutically effective amount is administered daily for the effective period of time. In certain implementations, the therapeutically effective amount is divided into two or more doses administered daily to the subject at periodic intervals.

In any of the foregoing aspects, the Helicobacteraceae organism may be a *Helicobacter* species. In some aspects, the *Helicobacter* spp. is *H. pylori*, and the compound may be an *H. pylori* enzyme inhibitor.

The foregoing and other objects, features, and advantages of the invention will become more apparent from the following detailed description, which proceeds with reference to the accompanying figures.

DETAILED DESCRIPTION

Figures 1A, 1B, 1C, 1D, 1E, 1F, 1G, 1H:
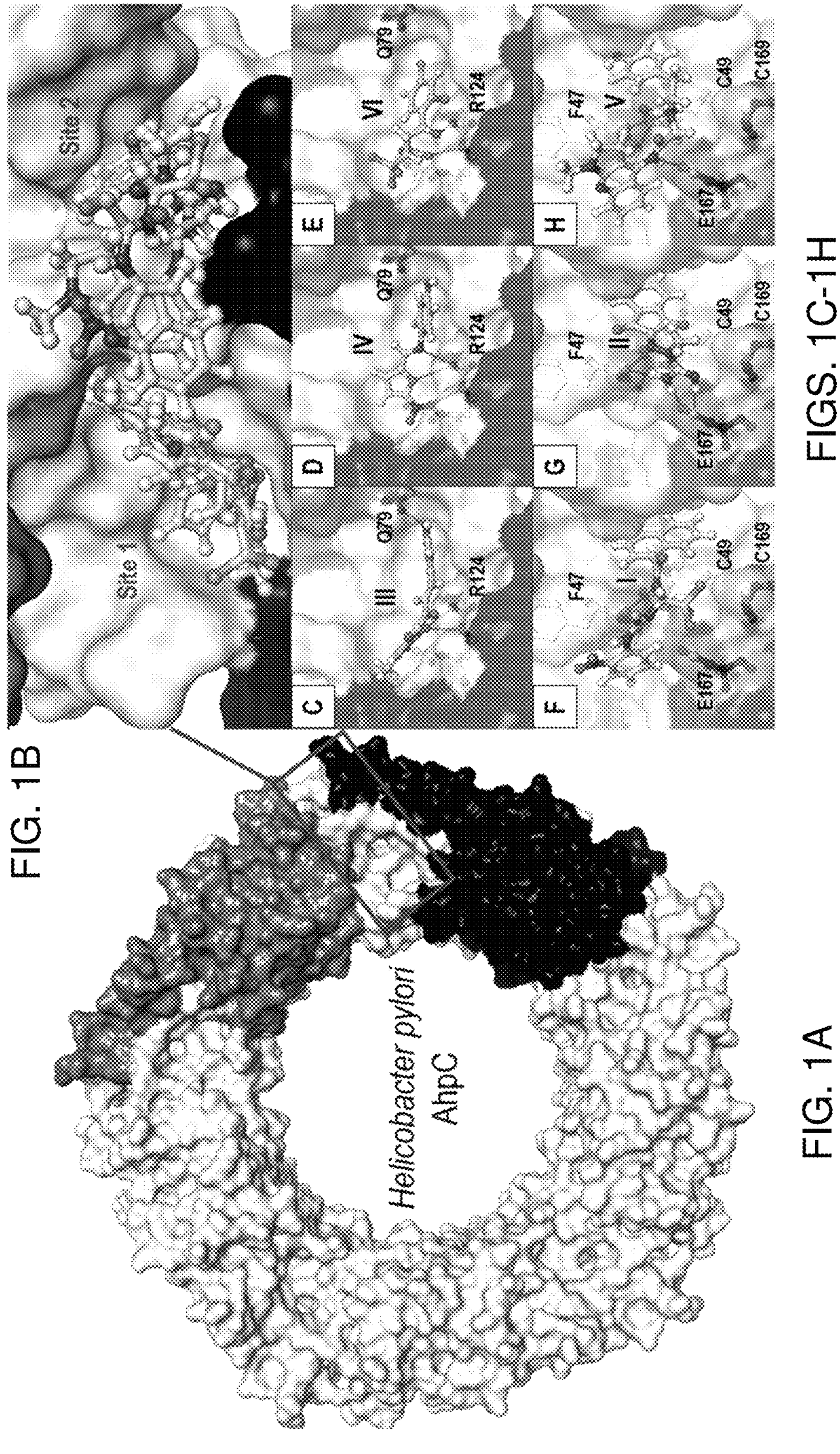
FIGS. 1A-1H show the drug target protein *H. pylori* AhpC (FIG. 1A), and the protein in complex with compounds I-VI (FIGS. 1B-1H). Key hydrogen bond interactions are depicted as magenta lines. Nearby amino acid residues involved in the peroxiredoxin catalytic conversion of hydroperoxides to water are noted.

This disclosure concerns pharmaceutical compositions comprising one or more Helicobacteraceae enzyme inhibitors, as well as methods of using the disclosed compositions to inhibit a Helicobacteraceae enzyme, thereby treating a Helicobacteraceae infection. In some aspects, the Helicobacteraceae organism is a *Helicobacter* spp., such as *Helicobacter pylori* (*H. pylori*).

Up to 50% of the human population is infected with *H. pylori* (Yamakoa, ed., *Helicobacter pylori*: Molecular Genetics and Cellular Biology, Caister Academic Press, 2008). *H. pylori* is a causative agent of stomach/duodenal ulcers and cancers. Stomach cancer is a devastating disease with a 5-yr survival rate in the US of 15% and is responsible for the deaths of nearly 800,000 people every year. More than 95% of stomach cancer is driven by a widespread bacterial stomach pathogen, *H. pylori*, which infects about half of the world's population. *H. pylori* is adept at avoiding natural elimination by the immune system, and infections can persist for decades leading to gastritis, ulcers, and adenocarcinomas. *H. pylori* is intrinsically resistant to many antimicrobials and to date there is no antibiotic therapy that guarantees successful eradication. In 2017 the World Health Organization declared *H. pylori* a 'high-priority' pathogen, for which the design of new antimicrobials is urgently required.

Bacteria can be attacked and killed by immune cells which introduce oxidizing molecules (such as hydroperoxides) that damage the bacterial cells. However, some bacteria, such as Helicobacteraceae organisms, can defend themselves by producing enzymes which catalyze reactions that destroy the oxidizing molecules through a process that converts them to harmless water or alcohols. The enzymes include peroxidases, such as peroxiredoxins. To perform this function, peroxiredoxin enzymes must alternate between two physical shapes, known as "conformations." During the peroxiredoxin enzyme's physical transformation of shape a temporary "pocket" forms in the enzyme structure. In some aspects, the enzymes are inhibited by compounds that bind to the pocket, locking the enzyme in its deformed state and preventing the enzyme from decomposing the oxidizing molecules. The pocket, and binding of several exemplary compounds disclosed herein, are depicted in FIGS. 1A-1H, respectively. The oxidizing molecules can then kill the bacterium, thereby treating a Helicobacteraceae infection. Left untreated, a Helicobacteraceae infection may cause gastric disease, colitis, hepatitis, or cancer (e.g., gastric cancer, liver cancer). For example, an untreated *H. pylori* infection may manifest as a duodenal and/or gastric ulcer, and/or a *H. pylori* infection may result in developing gastric cancer, such as gastric adenocarcinoma (e.g., non-cardia gastric adenocarcinoma) or gastric lymphoma (e.g., gastric mucosa-associated lymphoid tissue lymphoma).

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Definitions of common terms in chemistry may be found in Richard J. Lewis, Sr. (ed.), Hawley's Condensed Chemical Dictionary, published by John Wiley & Sons, Inc., 2016 (ISBN 978-1-118-43515-0). The presently disclosed compounds also include all isotopes of atoms present in the compounds, which can include, but are not limited to, deuterium, tritium, $^{18}F$, $^{14}C$, etc.

In order to facilitate review of the various embodiments of the disclosure, the following explanations of specific terms are provided:

AhpC: alkyl hydroperoxide reductase C

BCP: bacterioferritin comigratory protein

Effective amount: An amount of a compound or composition sufficient to achieve a particular desired result, such as to inhibit a protein or enzyme, particularly a peroxidase, such as a peroxiredoxin: to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

Helicobacteraceae: A family consisting of five genera—*Helicobacter, Sulfuricurvum, Sulfurimonas, Sulfurovutn, Thiovulum, and Wolinella*. The *Helicohacter* genus includes about 35 species, e.g., *H. pylori, H. heilmanii, H. cinaedi, H. fennelliae, H. westmaedii, H. rappini*, and *H. canadensis*, which are found in humans. The most common species found in humans is *H. pylori.*

Isomer: One of two or more molecules having the same number and kind of atoms, but differing in the arrangement or configuration of the atoms. Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture."

Parenteral administration: Any non-oral means of administration that bypasses the skin and mucous membranes, e.g., by injection (e.g., intravenous, intramuscular, subcutaneous) or infusion.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, $21^{st}$ Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Prx: peroxiredoxin

Solvate: A complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

Subject: An animal (human or non-human) subjected to a treatment, observation or experiment. Includes both human and veterinary subjects, including human and non-human mammals, such as rats, mice, cats, dogs, pigs, horses, cows, and non-human primates.

Therapeutically effective amount or dose: An amount sufficient to provide a beneficial, or therapeutic, effect to a subject or a given percentage of subjects.

Tpx: thiol-specific peroxidase

Treating or treatment: As used herein, these terms refer to ameliorating a disease or condition of interest in a patient or subject, particularly a human having the disease or condition of interest, and includes by way of example, and without limitation:

(i) inhibiting the disease or condition, for example, arresting or slowing its development;

(ii) relieving the disease or condition, for example, causing regression of the disease or condition or a symptom thereof; or (iii) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

II. Pharmaceutical Compositions

A pharmaceutical composition comprises a Helicobacteraceae enzyme inhibitor and a pharmaceutically acceptable carrier. In any of the following aspects, the Helicobacteraceae organism may be a *Helicobacter* spp. In some aspects, the *Helicobacter* spp. is *H. pylori*. and the Helicobacteraceae enzyme inhibitor is an *H. pylori* enzyme inhibitor.

In any of the foregoing or following embodiments, the pharmaceutical composition may be formulated for parenteral or oral administration. In certain implementations, the pharmaceutical composition is an oral formulation. The oral formulation may be a liquid, suspension, or solid dosage form. In some examples, the pharmaceutical composition is formulated into oral dosage form, such as a solid dosage form, for oral administration.

An oral dosage form may be formulated to release the enzyme inhibitor in a subject's stomach and/or duodenum. In some embodiments, the oral dosage form further comprises a coating or a capsule shell encapsulating the pharmaceutical composition, wherein the coating or capsule shell is an immediate release coating or capsule shell formulated to dissolve in the subject's stomach and/or duodenum. Suitable coatings or capsule shells may comprise a polysaccharide, a vinyl alcohol polymer, an acrylic polymer, gelatin, or any combination thereof. In some implementations, the coating or capsule shell comprises hydroxypropyl methylcellulose (HPMC), hydroxypropyl cellulose (HPC), hydroxyethyl cellulose (HEC), methylcellulose (MC), sodium carboxymethyl cellulose (NaCMC), polyvinyl alcohol (PVA), polyvinylpyrrolidone (PVP), polyethylene glycol (PEG), a PVP-PVA copolymer, a PVA-polyethylene glycol (PEG) copolymer, a dimethylaminoethyl methacrylate/butyl methacrylate/methyl methacrylate (2:1:1) copolymer, gelatin, pullulan, or any combination thereof.

In any of the foregoing or following embodiments, the enzyme inhibitor may be a peroxidase inhibitor, such as a peroxiredoxin inhibitor. In some embodiments, the peroxiredoxin is AhpC, Tpx, BCP, or any combination thereof. In some implementations, the enzyme inhibitor has a size, shape, and/or composition complementary to a structural pocket formed by the enzyme when it undergoes a conformational change during a catalytic reaction.

In some embodiments. the enzyme inhibitor is a compound, or a stereoisomer or pharmaceutically acceptable salt, solvate or hydrate thereof, wherein the compound has a structure according to formula I', formula II', formula ET, compound IV, formula V', formula VI':

(I')

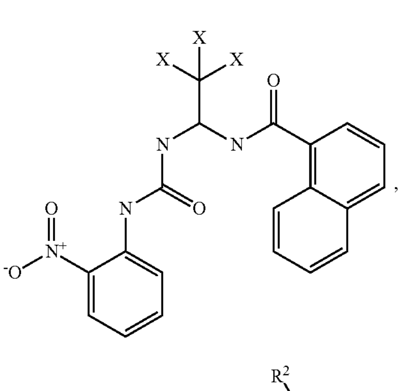

, (II')

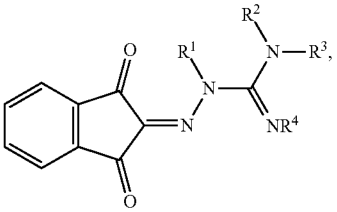

-continued (III')

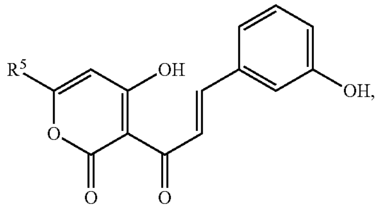

(IV)

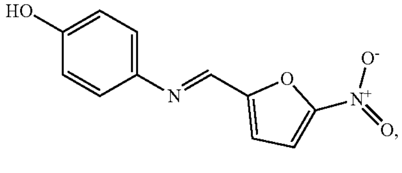

(V')

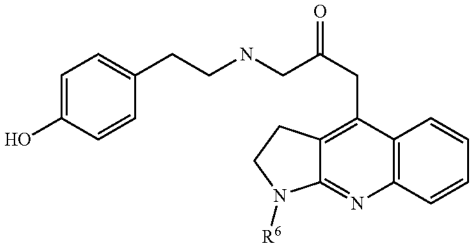

(VI')

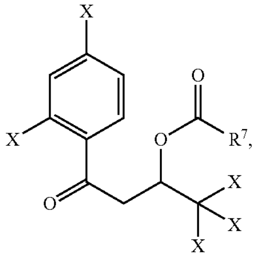

where each X independently is halo (Cl, F, Br, or I); and $R^1$-$R^7$ independently are H or $C_1$-$C_5$ alkyl. In one implementation, each X on compound I' is the same halogen. In another implementation, each X on compound VI' is the same halogen. In certain aspects, each X is Cl. In some implementations, the compound has a structure according to formula II' where $R^1$ is $C_1$-$C_5$ alkyl and $R^2$-$R^4$ are H. In certain implementations, $R^1$ is methyl and $R^2$-$R^4$ are H. In some aspects, the compound has a structure according to formula III', formula V', or formula V' where $R^5$-$R^7$ independently are $C_1$-$C_5$ alkyl. In certain aspects, $R^5$, $R^6$, and/or $R^7$ is methyl.

In some embodiments, the enzyme inhibitor is a compound, or a stereoisomer or pharmaceutically acceptable salt, solvate or hydrate thereof, wherein the compound is compound I, compound II, compound III, compound IV, compound V, compound VI, or any combination thereof:

(I)

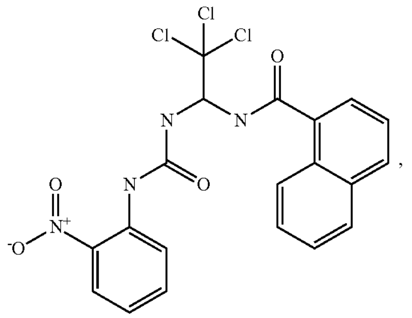

(II)

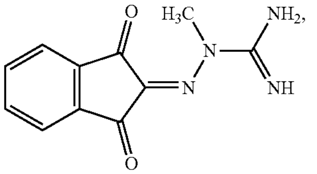

(III)

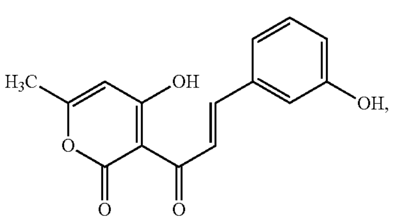

(IV)

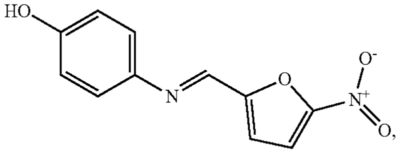

(V)

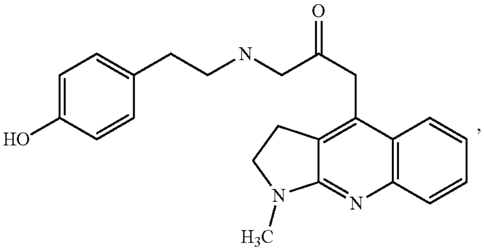

(VI)

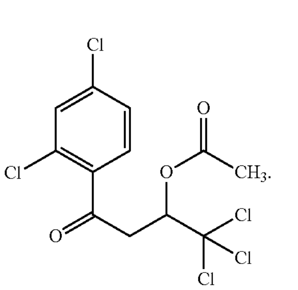

In some embodiments, compound I is a stereoisomer IA and/or compound VI is a stereoisomer VIA:

(IA)

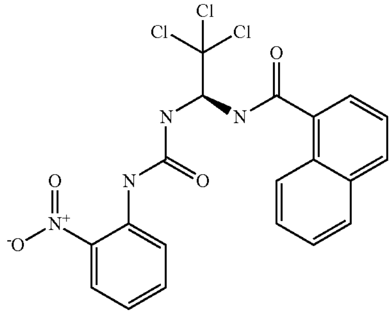

(VIA)

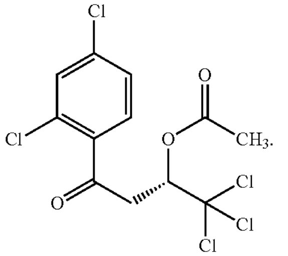

In any of the foregoing or following embodiments, the enzyme inhibitor may be a compound according to formula I', formula II', or a combination thereof. In some embodiments, the enzyme inhibitor is compound I, compound II, or a combination thereof. In such embodiments, the pharmaceutical composition comprises compound I, compound II, or a combination thereof, and a pharmaceutically acceptable carrier. In certain implementations, the enzyme inhibitor is compound IA, compound II, or a combination thereof.

In any of the foregoing or following embodiments, the enzyme inhibitor may be added to the pharmaceutical composition in the form of a salt, a solvate, or a hydrate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and b-glycerophosphate. Suitable inorganic salts may also be formed, including hydrochloride, halide, sulfate, nitrate, bicarbonate, and carbonate salts. The salts may be obtained using procedures known to persons of ordinary skill in the art, for example by reacting a sufficiently basic compound, such as an amine, with a suitable acid to provide a physiologically acceptable ionic compound. Alkali metal (for example, sodium, potassium or lithium) or alkaline earth metal (for example, calcium) salts of carboxylic acids can also be prepared by analogous methods.

The disclosed pharmaceutical compositions may be administered to a subject, such as a human or veterinary patient, in a variety of forms. The forms can be specifically adapted to a chosen route of administration, e.g., oral or parenteral administration (e.g., intravenous, intramuscular, or subcutaneous routes).

The Helicobacteraceae enzyme inhibitor compounds described herein may be systemically administered in combination with a pharmaceutically acceptable carrier, such as an inert diluent or an assimilable edible carrier. For oral administration, the enzyme inhibitors can be enclosed in hard or soft shell capsules, compressed into tablets, or a pharmaceutical composition comprising the enzyme inhibitor can be incorporated directly into the food of a subject's diet. The enzyme inhibitors also may be combined with one or more excipients and used in the form of ingestible tablets, buccal tablets, troches, capsules, elixirs, suspensions, syrups, wafers, and the like. Such compositions and preparations typically contain at least 0.1 wt % of the enzyme inhibitor. The percentage of the compositions and preparations can vary and may conveniently be from about 2% to about 60% of the weight of a given unit dosage form. The amount of enzyme inhibitor in such therapeutically useful compositions is such that an effective dosage level can be obtained.

The tablets, troches, pills, capsules, and the like may also contain one or more of the following excipients: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with an immediate release coating as described above. A syrup or elixir may contain the active compound, sucrose or fructose as a sweetening agent, methyl and propyl parabens as preservatives, a dye and flavoring such as cherry or orange flavor. Any material used in preparing a unit dosage form should be pharmaceutically acceptable and substantially non-toxic in the amounts employed. In addition, the enzyme inhibitor may be incorporated into sustained-release preparations and devices.

The enzyme inhibitor may be administered by any suitable route. In some aspects, the enzyme inhibitor is administered intravenously or intraperitoneally by infusion or injection. Solutions of the enzyme inhibitor or its salts, solvates, or hydrates, can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the enzyme inhibitor. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the enzyme inhibitor in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the enzyme inhibitor plus any additional desired ingredient present in the previously sterile-filtered solutions.

Useful dosages of the enzyme inhibitors described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of an enzyme inhibitor, or an active salt, solvate, or hydrate thereof, required for use in treatment will vary not only with the particular enzyme inhibitor (or salt, solvate, or hydrate thereof) selected but also according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the enzyme inhibitor for eliciting the desired activity or biological response in the subject, and will be ultimately at the discretion of an attendant physician or clinician.

Dosage regimens can be adjusted to provide an optimum therapeutic response. A therapeutically effective amount is also one in which any toxic or detrimental side effects of the enzyme inhibitor is outweighed in clinical terms by therapeutically beneficial effects. A non-limiting range for a therapeutically effective amount of an *H. pylori* enzyme inhibitor within the methods and formulations of the disclosure is mg/kg body weight to 100 mg/kg body weight, such as 0.01 mg/kg body weight to 20 mg/kg body weight, 0.05 mg/kg to 5 mg/kg body weight, or 0.2 mg/kg to 2 mg/kg body weight. Dosage can be varied by the attending clinician to maintain a desired concentration at a target site (for example, in the stomach or duodenum). Higher or lower concentrations can be selected based on the mode of delivery, for example, oral delivery versus intravenous or subcutaneous delivery.

III. Methods of Use

Host immune cells may kill invading bacteria by producing cytotoxic hydroperoxides, such as $H_2O_2$. However, at least some Helicobacteraceae organisms have an especially robust enzyme defense system that eliminates $H_2O_2$ by rapidly converting it to water. The enzyme produced by the Helicobacteraceae organism may be a peroxidase, such as a peroxiredoxin. Due to the enzyme defense system, the Helicobacteraceae organisms are adept at avoiding natural elimination by the immune system and infections can persist for decades. In some instances, a persistent infection leads to gastritis, ulcers, and/or adenocarcinomas.

In any of the foregoing or follow aspects, the Helicobacteraceae organism may be a *Helicobacter* spp. In certain aspects, the *Helicobacter* spp. is *H. pylori. H. pylori* is intrinsically resistant to many antimicrobials and to date there is no antibiotic therapy that guarantees successful eradication.

Embodiments of the disclosed compounds are Helicobacteraceae peroxiredoxin enzyme inhibitors. The peroxidase enzymes produced by a Helicobacteraceae organism enable it to survive inside a subject's stomach. In some embodiments, inhibiting the Helicobacteraceae enzyme allows the hydroperoxides produced by the host's immune system to inhibit growth of the Helicobacteraceae organism and/or eradicate a Helicobacteraceae infection. In any of the foregoing or following aspects, the compound may be a *H. pylori* enzyme inhibitor.

In one implementation, an enzyme produced by a Helicobacteraceae organism is inhibited by contacting the enzyme with an effective amount of a compound, or a stereoisomer, or pharmaceutically acceptable salt, solvate or hydrate thereof, the compound having a structure according to formula I', formula II', formula III', compound IV, formula V', formula VI', or any combination thereof. In some aspects, the compound is compound I, compound II, compound III, compound IV, compound V, compound VI, or any combination thereof. In some examples, compound I is the stereoisomer compound IA and/or compound VI is the stereoisomer compound VIA. In certain examples, the enzyme is contacted by compound I (or compound IA), compound or a combination thereof.

In some embodiments, a method for ameliorating a Helicobacteraceae infection comprises administering to a subject a therapeutically effective amount of a pharmaceutical composition as disclosed herein. The pharmaceutical composition may be formulated as an oral or parenteral dosage form.

In some examples, the subject is identified as having a Helicobacteraceae infection prior to administering the therapeutically effective amount of the pharmaceutical composition. The subject may be identified on the basis of signs/symptoms and/or diagnostic tests. Signs and symptoms of a Helicobacteraceae infection and/or cancer caused by a Helicobacteraceae infection include, but are not limited to, abdominal discomfort or swelling (e.g., stomach pain, bloating), nausea, unexplained weight loss, vomiting, burping, poor appetite, blood in the stool, early feeling of fullness while eating, fatigue, weakness, and combinations thereof. Diagnostic tests for the presence of a Helicobacteraceae organism and/or cancer caused by a Helicobacteraceae infection include, but are not limited to, blood tests (e.g., antibodies to the Helicobacteraceae organism); stool test (presence of Helicobacteraceae organisms); breath test (abnormal carbon dioxide levels are evidence of a Helicobacteraceae infection), endoscopy, and combinations thereof. In any of the foregoing or following aspects, the Helicobacteraceae organism may be *H. pylori.*

In any of the foregoing or following embodiments, the Helicobacteraceae enzyme may be a peroxidase. In some embodiments, the enzyme is peroxiredoxin (Prx). In certain examples, the Prx is AhpC, Tpx, BCP, or any combination thereof. In any of the foregoing or following embodiments, the Helicobacteraceae enzyme inhibitor may be a compound, or a stereoisomer or pharmaceutically acceptable salt, solvate, or hydrate thereof, having a structure according to formula I', formula II', formula compound IV, formula V', formula VI', or any combination thereof. In some embodiments, the enzyme inhibitor is compound I (or compound IA), compound II, compound III, compound IV, compound V, compound VI (or compound VIA), or any combination thereof. In some embodiments, the enzyme inhibitor is compound I or compound II. In certain implementations, the enzyme inhibitor is compound IA or compound II.

In any of the foregoing or following embodiments, the therapeutically effective amount is administered at periodic intervals for an effective period of time to ameliorate the Helicobacteraceae infection. Ameliorating the infection may comprise (i) eradicating the Helicobacteraceae infection in the subject; or (ii) producing a negative result on a Helicobacteraceae test performed after the subject has been administered the pharmaceutical composition; or (iii) reducing or eliminating one or more symptoms of the Helicobacteraceae infection in the subject; or (iv) any combination of two or more of (i), (ii), and (iii). In some embodiments, the therapeutically effective amount is administered daily for the effective period of time. In some dosing regimens, the therapeutically effective amount is divided into two or more doses administered daily to the subject at periodic intervals.

In any of the foregoing or following embodiments, the method may further include co-administering an additional therapeutic agent. In some embodiments, the additional therapeutic agent is an antibiotic (e.g., amoxicillin, clarithromycin, levofloxacin, metronidazole, tetracycline, tinidazole, and combinations thereof), a proton pump inhibitor (e.g., omeprazole, esomeprazole, lansoprazole, pantoprazole, dexlansoprazole, rabeprazole, vonoprazan, and the like), bismuth subsalicylate, bismuth citrate, a histamine (H-2) blocker (e.g., cimetidine, famotidine, nizatidine, and the like), or any combination thereof. If the subject has cancer resulting from a Helicobacteraceae infection, the additional therapeutic agent may comprise a chemotherapeutic agent and/or radiation therapy. The Helicobacteraceae enzyme inhibitor and the additional therapeutic agent may be co-administered simultaneously or sequentially in any order. If administered simultaneously, the Helicobacteraceae enzyme inhibitor and the additional therapeutic agent may be administered together in a single pharmaceutical composition, or the Helicobacteraceae enzyme inhibitor and additional therapeutic agent may be administered in separate pharmaceutical compositions by the same or different routes of administration.

IV. Examples

Example 1

Screening Assays

Protein crystallography was used to determine the molecular structure of conformational changes that *H. pylori* Prx undergoes during its catalytic cycle of hydroperoxide reduction. Crystallography revealed a temporary structural "pocket" that forms in the protein during catalysis. The pocket exhibits features suitable for drug binding and will allow specific targeting of IL *pylori* Prx. On a standard scoring system developed by Merck, which ranges from negative (unpromising) to 0.5+(druggable), the *H. pylori* pocket scored as 0.62.

Virtual ligand screening (VLS) was performed on four million drug-like compounds with Molsoft® internal coordinate mechanics (ICM) modeling software (Molsoft LLC, San Diego, CA). The VLS identified approximately 200 compounds appeared to have a shape and chemical complementarity to the *H. pylori* Prx pocket (FIG. 1A). Compounds I-VI are presumed to directly bind H. pylon AhpC (FIGS. 1B-1H) with dissociation constants of −15, −15, −19, −17, −16, and −14 kcal/mol, respectively. Compounds were screened experimentally for inhibition of AhpC enzymatic activity in vitro using the following method.

Tris(2-carboxyethyl)phosphine hydrochloride (TCEP)-coated beads were washed 3×. For each washing, 150 μL of the beads were dispensed into a centrifuge tube, and 850 μL of buffer (25 mM potassium phosphate, 1 mM EDTA, pH 7)

was added, followed by centrifugation at 1500 rcf for 60 seconds. After the third wash, 75 μL of buffer was added to the beads.

The following reagents were prepared:

1. 25 μM AhpC (alkyl hydroperoxide reductase C)—652.47 μlL buffer, 39 μL washed TCEP beads, 88.5 μL concentrated AhpC protein.
2. 250 μM TrxA (thioredoxin A)—427 μL buffer, 39 μL washed TCEP beads, 314 μL concentrated TrxA protein.
3. 25 μM TrxR (thioredoxin R)—732.81 μL buffer, 39 μL washed TCEP beads, 8.19 μL concentrated TrxR protein.
4. 100 μM iodoacetamide in DMSO.
5. 1 mM hydrogen peroxide in $H_2O$.

The prepared reagents 1-3 were incubated for 1 hour at room temperature and then centrifuged. The reduced proteins were extracted and transferred to new tubes.

A reaction mix was prepared by combining 17.136 mL buffer, 201.6 μL 25 μM TrxR, 201.6 μL 250 μM TrxA, and then adding 2.016 mL 1 mM $H_2O_2$ and 201.6 μL 15 mM NADPH. Aliquots, 196 μL, of the reaction mix were added to wells of a microplate.

Compounds to be screened, 2 μL, were added to individual wells. Absorbance at 340 nm was monitored for up to 10 minutes, or until reaction curves became linear. Once absorbance stabilized, 2 μL of the 25 μM AhpC solution was added to the wells. A negative control was prepared by adding 2 μL to a well containing the reaction mixture. Positive controls were prepared by adding 2 μL of AhpC solution to two wells that contained the reaction mixture. Absorbance was then monitored at 340 nm for 1.5 hours. Three replicates were run for each compound, negative control, and positive control. Promising compound candidates were evaluated at 400 μM and 40 μM final concentrations.

Figure 2B:
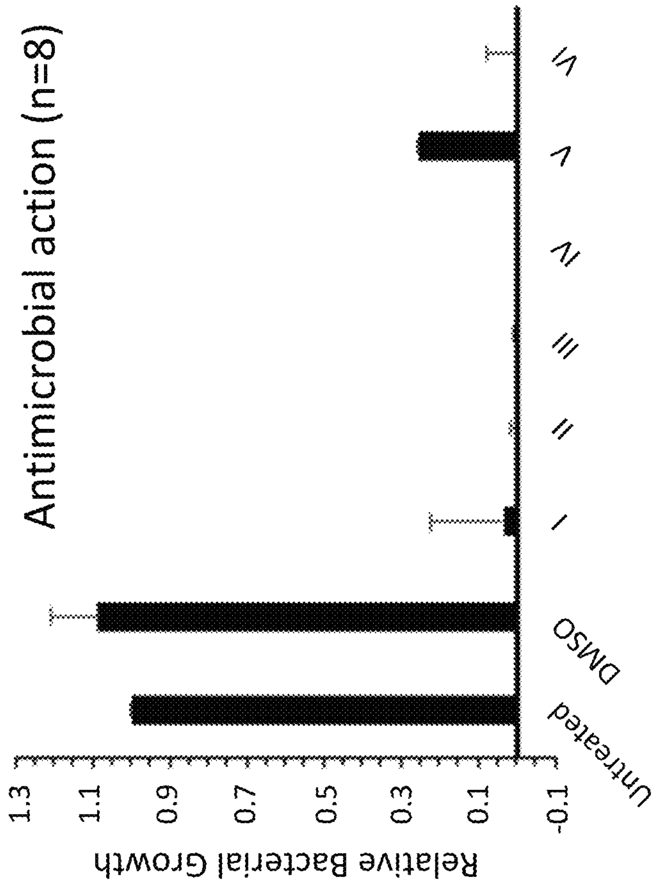
FIGS. 2A-2B show the antimicrobial activity of a representative compound against *H. pylori*, compound IV, relative to bacterial growth with a control treatment lacking inhibitor (FIG. 2A) and a bar graph showing the antimicrobial activity of repeated experiments with compounds I-VI (FIG. 2B). Error bars shown are standard error of the mean for eight replicates.
Figure 2A:
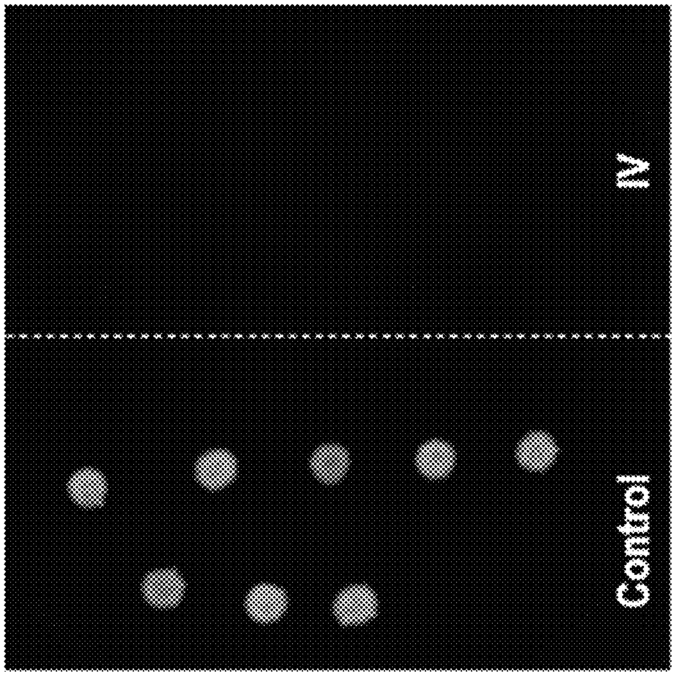

Promising compound candidates (those that exhibited >75% inhibition of AhpC activity) were evaluated in a blood plate screening assay to test lethality against *H. pylori* strain GFP-G27. This assay determines bacterial growth in the presence or absence of the compound relative to control treatments. The *H. pylori* GFP-G27 strain is a clinical isolate engineered to express green fluorescence protein (GFP) with an engineered kanamycin resistance gene (KanR) to serve as a tool for growing cultures that contain only this specific bacterium. Blood plates were inoculated with *H. pylori* strain GIT-G27 and allowed to grow three days in 10% $CO_2$. The cells were then inoculated in brucella broth supplemented with 10% fetal bovine serum ($BB_{10}$ media)+50 μg/ml kanamycin for a starter culture. Lethality was determined by adding 2 μl of compound dissolved in DMSO, to *H. pylori* cells in a 20 μl volume, such that the compound was at 500 μM final concentration and the cells were at a final $OD_{600}$ of 0.125. Experiments were compared to controls where cells were untreated, or treated with 2 μl DMSO. From each experiment, 2 μl of solution was spotted onto a fresh blood plate and allowed to incubate for 48 hours growing with 10% $CO_2$. Eight individual experiments were performed for each treatment. Bacteria growth was determined by quantifying GFP fluorescence for each treatment area, relative to the growth of the untreated bacterial samples. The results are shown in FIGS. 2A-2B.

The purpose of the foregoing assays was to determine to what extent compounds I-VI inhibit the growth of *H. pylori*. Compounds I-VI substantially inhibited the growth, or were completely lethal, to *H. pylori* (FIG. 2).

Example 2

Therapeutic Uses

A subject having, or suspected of having, a Helicobacteraceae infection is administered a therapeutically effective amount of a pharmaceutical composition as disclosed herein. In some examples, the subject has gastritis, a gastric or duodenal ulcer, or a gastric or duodenal cancer. The subject may be identified as having a Helicobacteraceae infection on the basis of laboratory testing (e.g., blood, stool, and/or breath tests) and/or diagnostic imaging (e.g., upper endoscopy). In some implementations, the subject is suspected of having a Helicobacteraceae infection on the basis of one or more symptoms characteristic of a Helicobacteraceae infection, including but not limited to abdominal discomfort or swelling (e.g., stomach pain, bloating), nausea, unexplained weight loss, vomiting, burping, poor appetite, blood in the stool, early feeling of fullness while eating, fatigue, weakness, and combinations thereof.

In any of the foregoing examples, the subject may be administered the therapeutically effective amount of the pharmaceutical composition at periodic intervals for an effective period of time to ameliorate at least one sign or symptom characteristic of a Helicobacteraceae infection. For example, the subject may be administered the therapeutically effective amount of the pharmaceutical composition once daily or in divided doses over the course of a day, such as 2-3 divided doses per day. The therapeutically effective amount may be determined by a clinician based on factors including, but not limited to, subject age, subject weight, infection severity, infection duration, the presence of an ulcer or a cancer, and combination thereof. The pharmaceutical composition is administered by any suitable route including, but not limited to, parenterally (e.g., intravenously, intramuscularly, subcutaneously) or orally.

In some embodiments, administration of a therapeutically effective dose of a compound as disclosed herein to a subject produces at least a 5% reduction in at least one sign or symptom characteristic of a Helicobacteraceae infection in the subject, such as at least a 10% reduction, at least a 20% reduction, at least 30% reduction, at least 40% reduction, at least 50% reduction, at least 60% reduction, at least 70% reduction, at least 80% reduction, or at least 90% reduction in at least one sign or symptom characteristic of a Helicobacteraceae infection. In some instances, administration is continued until at least one sign or symptom consistent with an *H. pylori* infection are eliminated, or until the Helicobacteraceae infection is eradicated as determined by laboratory testing and/or diagnostic imaging. In certain cases, administration may continue for a period of time after signs and symptoms consistent with a Helicobacteraceae infection have ceased. In any of the foregoing embodiments, the Helicobacteraceae infection may be an *H. pylori* infection.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. An oral dosage form comprising an immediate release coating or capsule shell formulated to dissolve in a subject's stomach and/or duodenum, wherein the immediate release coating or capsule shell encapsulates a Helicobacteraceae enzyme inhibitor and a pharmaceutically acceptable carrier, and wherein the Helicobacteraceae enzyme inhibitor is selected from (i)

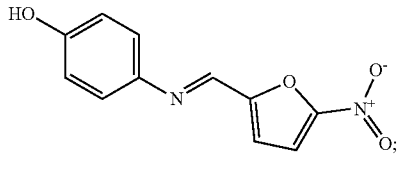 [SMILES: O=[N+]([O-])c1ccc(/C=N/c2ccc(O)cc2)o1]

(ii) a compound having a structure according to Formula I', II', III', V', or VI';

(iii) a stereoisomer, pharmaceutically acceptable salt, solvate, or hydrate of (i) or (ii); or (iv) any combination of two or more of (i)-(iii), wherein Formulas I', II', III', V', and VI' are (I')

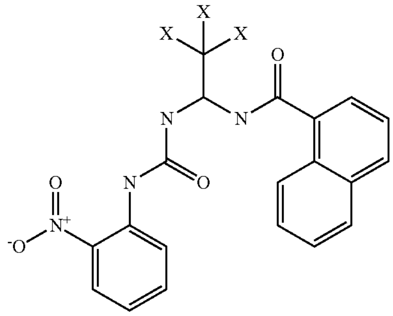

, (II')

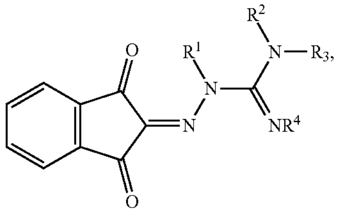

(III')

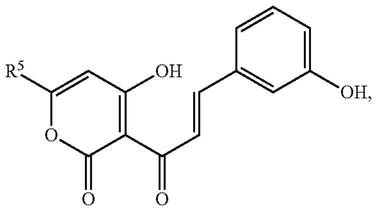

(V')

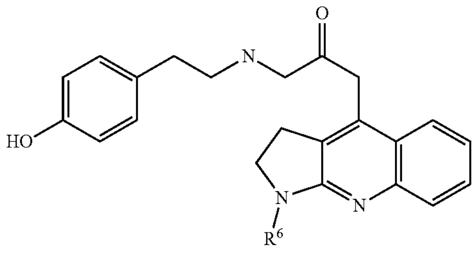

,

-continued (VI')

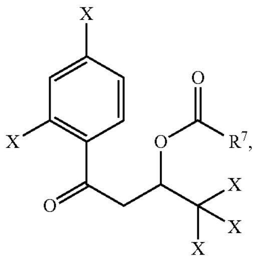

wherein each X independently is halo, and $R^1$—$R^7$ independently are H or $C_1$—$C_5$ alkyl.

2. The oral dosage form of claim 1, wherein the coating or capsule shell comprises a polysaccharide, a vinyl alcohol polymer, an acrylic polymer, gelatin, or any combination thereof.

3. The oral dosage form of claim 1, wherein the coating or capsule shell comprises hydroxypropyl methylcellulose (HPMC), hydroxypropyl cellulose (HPC), hydroxyethyl cellulose (HEC), methylcellulose (MC), sodium carboxymethyl cellulose (NaCMC), polyvinyl alcohol (PVA), polyvinylpyrrolidone (PVP), polyethylene glycol (PEG), a PVP-PVA copolymer, a PVA-polyethylene glycol (PEG) copolymer, a dimethylaminoethyl methacrylate/butyl methacrylate/methyl methacrylate (2:1:1) copolymer, gelatin, pullulan, or any combination thereof.

4. The oral dosage form of claim 1, wherein the Helicobacteraceae enzyme inhibitor is a peroxiredoxin inhibitor.

5. The oral dosage form of claim 4, wherein the peroxiredoxin inhibitor inhibits alkyl hydroperoxide reductase C (AhpC), thiol-specific peroxidase (Tpx), bacterioferritin comigratory protein (BCP), or any combination thereof.

6. The oral dosage form of claim 1, wherein the Helicobacteraceae enzyme inhibitor is a *Helicobacter pylori* enzyme inhibitor.

7. The oral dosage form of claim 1, wherein the compound is selected (I')

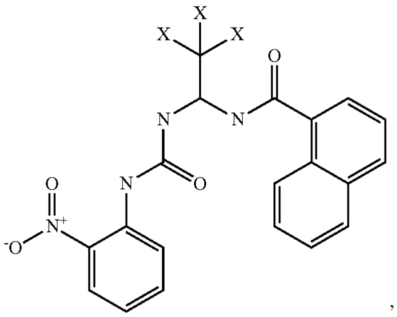

, (II')

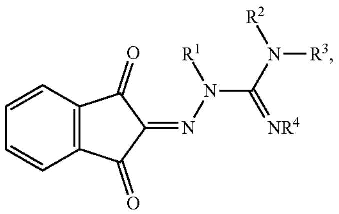

-continued (III')

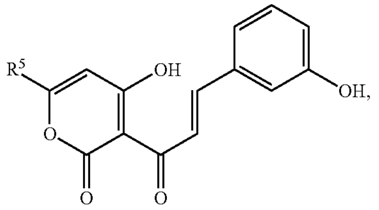

(IV')

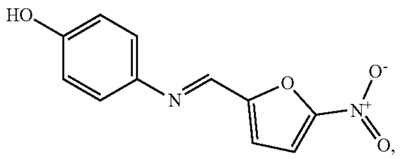

(V')

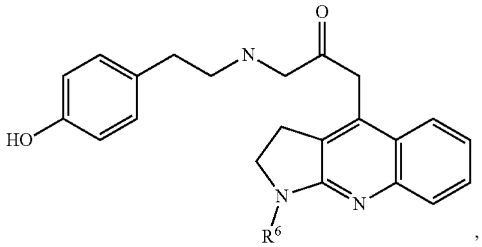

, (VI')

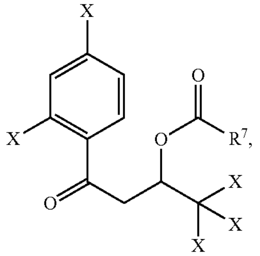

from (III), or any combination thereof.

8. The oral dosage form of claim 1, wherein the compound is selected from (compound IA)

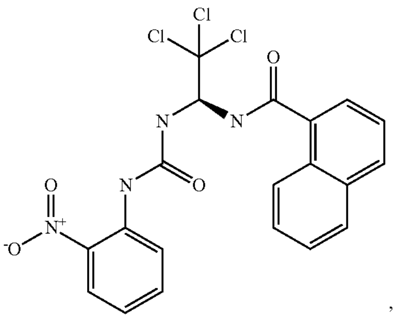

, (compound II)

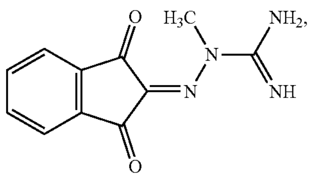

or a combination thereof.

9. A method for ameliorating *Helicobacter pylori* infection, comprising administering a therapeutically effective amount of an oral dosage form to a subject having, or suspected of having, *Helicobacter pylori* infection, wherein the oral dosage form comprises an immediate release coating or capsule shell formulated to dissolve in the subject's stomach and/or duodenum, wherein the immediate release coating or capsule shell encapsulates a Helicobacteraceae enzyme inhibitor and a pharmaceutically acceptable carrier, and wherein the Helicobacteraceae enzyme inhibitor is selected from (i)

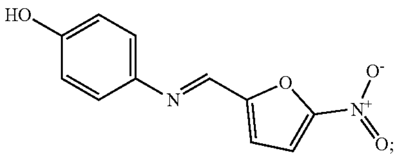 [SMILES: O=[N+]([O-])c1ccc(/C=N/c2ccc(O)cc2)o1]

(ii) a compound having a structure according to Formula I', II', III', V', or VI';

(iii) a stereoisomer, pharmaceutically acceptable salt, solvate, or hydrate of (i) or (ii); or (iv) any combination of two or more of (i)-(iii), wherein Formulas I', II', III', V', and VI' are (I')

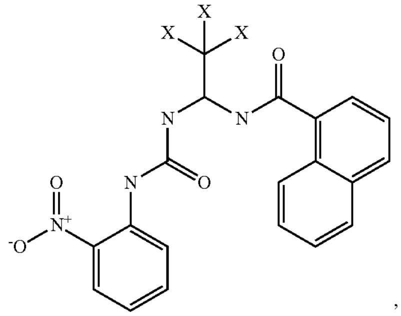

, (II')

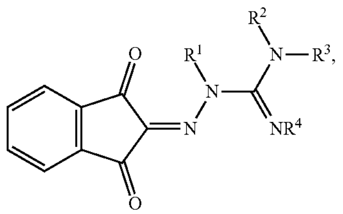

(III')

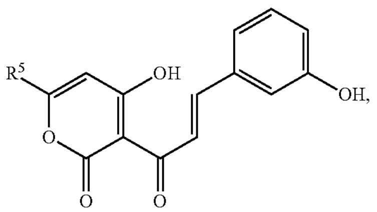

-continued (V')

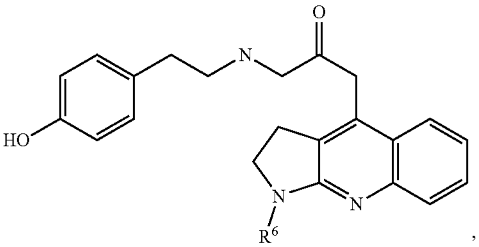

, (VI')

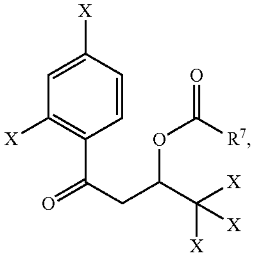

wherein each X independently is halo, and $R^1$-$R^7$ independently are H or $C_1$-$C_5$ alkyl.

10. The method of claim 9, wherein the Helicobacteraceae enzyme inhibitor is a peroxiredoxin inhibitor.

11. The method of claim 9, wherein the Helicobacteraceae enzyme inhibitor is selected from (I)

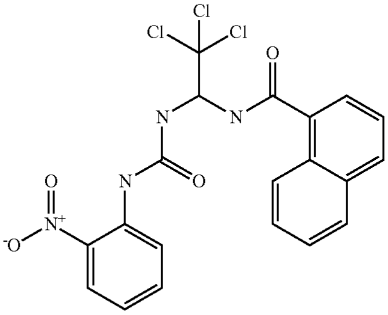

, (II)

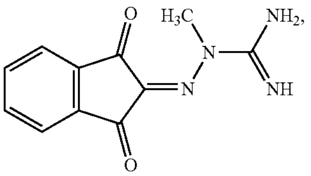

(III)

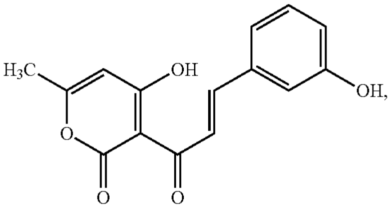

-continued (V)

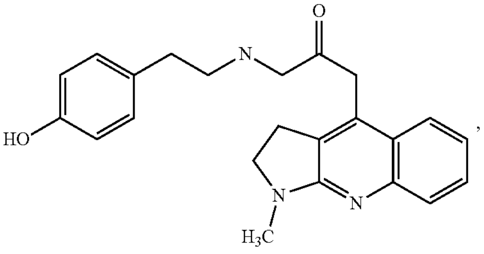

, (VI)

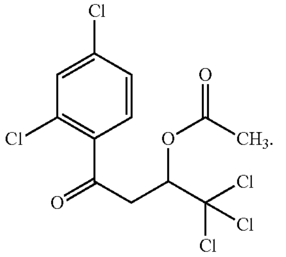

or any combination thereof.

12. The method of claim 9, wherein the therapeutically effective amount is administered at periodic intervals for an effective period of time to ameliorate the *Helicobacter pylori* infection.

13. A method, comprising inhibiting an enzyme produced by *Helicobacter pylori* by contacting the enzyme with an effective amount of an oral dosage form comprising an immediate release coating or capsule shell formulated to dissolve in a subject's stomach and/or duodenum, wherein the immediate release coating or capsule shell encapsulates a Helicobacteraceae enzyme inhibitor and a pharmaceutically acceptable carrier, and wherein the Helicobacteraceae enzyme inhibitor is selected from (i)

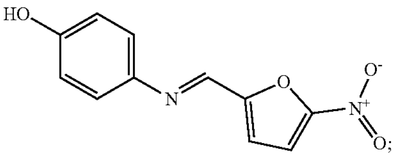 [SMILES: O=[N+]([O-])c1ccc(/C=N/c2ccc(O)cc2)o1]

(ii) a compound having a structure according to Formula I', II', III', V', or VI';

(iii) a stereoisomer, pharmaceutically acceptable salt, solvate, or hydrate of (i) or (ii); or (iv) any combination of two or more of (i)-(iii), wherein Formulas I', II', III', V', and VI' are (I')

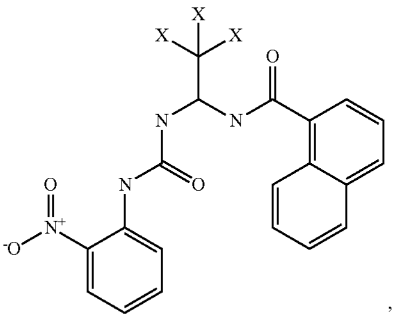

, (II')

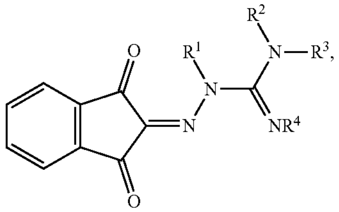

(III')

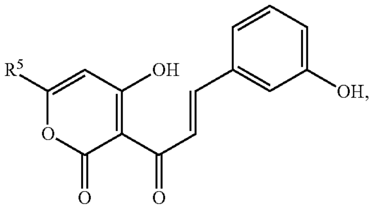

(V')

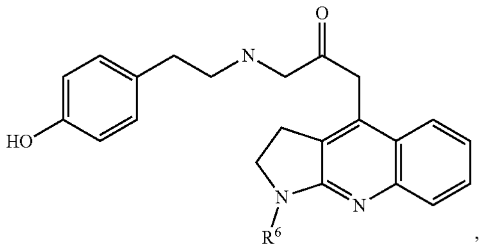

, (VI')

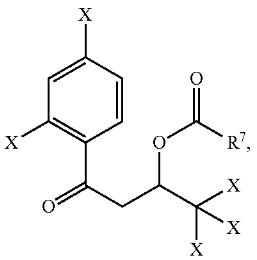

wherein each X independently is halo, and $R^1$-$R^7$ independently are H or $C_1$-$C_5$ alkyl.

14. The method of claim 13, wherein the Helicobacteraceae enzyme inhibitor is selected from (I)

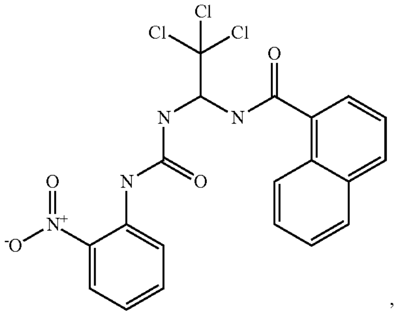

, (II)

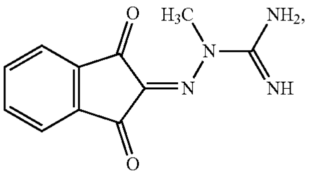

(III)

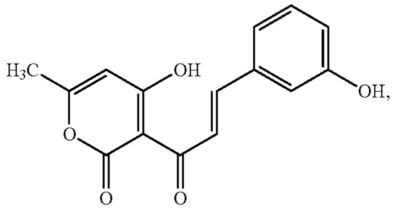

(IV)

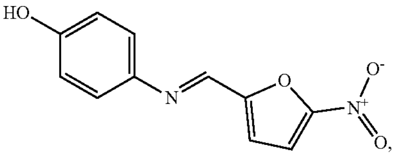

(V)

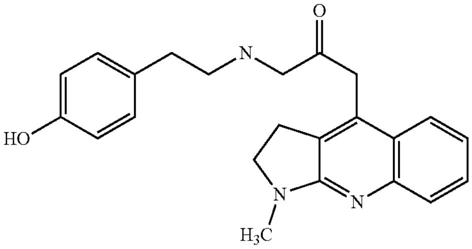

, (VI)

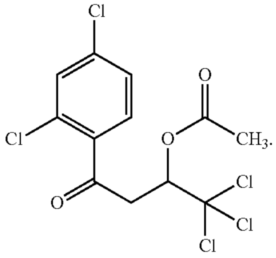

or any combination thereof.

15. The method of claim 13, wherein contacting is performed in vivo.

16. The method of claim 13, wherein the enzyme is a peroxiredoxin.

* * * * *